United States Patent
Sharon et al.

(10) Patent No.: US 8,591,505 B2
(45) Date of Patent: Nov. 26, 2013

(54) CRYOSURGICAL INSTRUMENT WITH REDIRECTED FLOW

(75) Inventors: Assaf Sharon, Tel Aviv (IL); Nir Berzak, Givataim (IL); Ron Hilleli, Zichron Yaacov (IL)

(73) Assignee: Icecure Medical Ltd., Caesarea (IL)

(*) Notice: Subject to any disclaimer, the term of this patent is extended or adjusted under 35 U.S.C. 154(b) by 71 days.

(21) Appl. No.: 13/339,506

(22) Filed: Dec. 29, 2011

(65) Prior Publication Data
US 2012/0232543 A1 Sep. 13, 2012

Related U.S. Application Data

(60) Provisional application No. 61/450,746, filed on Mar. 9, 2011.

(51) Int. Cl.
*A61B 18/02* (2006.01)
(52) U.S. Cl.
USPC .......................................................... 606/23
(58) Field of Classification Search
USPC ........................................ 606/20–26; 62/293
See application file for complete search history.

(56) References Cited

U.S. PATENT DOCUMENTS

| | | | | |
|---|---|---|---|---|
| 4,946,460 A | * | 8/1990 | Merry et al. | 606/24 |
| 5,716,353 A | * | 2/1998 | Matsuura et al. | 606/22 |
| 5,800,487 A | * | 9/1998 | Mikus et al. | 607/105 |
| 7,485,117 B2 | * | 2/2009 | Damasco et al. | 606/20 |
| 2002/0128698 A1 | | 9/2002 | Dobak, III et al. | |
| 2003/0055421 A1 | | 3/2003 | West et al. | |
| 2004/0172109 A1 | * | 9/2004 | Nest et al. | 607/96 |
| 2006/0135953 A1 | | 6/2006 | Kania et al. | |
| 2006/0235375 A1 | * | 10/2006 | Littrup et al. | 606/21 |
| 2009/0234345 A1 | * | 9/2009 | Hon | 606/21 |
| 2010/0241112 A1 | | 9/2010 | Watson | |

* cited by examiner

*Primary Examiner* — Michael Peffley
*Assistant Examiner* — Thomas Giuliani
(74) *Attorney, Agent, or Firm* — The Law Office of Michael E. Kondoudis

(57) ABSTRACT

A cryosurgical instrument that includes: an external shaft with a cryotip; a heat exchanger that cools a portion of the external shaft and the tip when cryogen is received thereby; and a flow diverter that receives a flow of cryogen, that splits the received flow of cryogen into two or more split cryogen flows, and that delivers the split cryogen flows to the heat exchanger, the flow diverter including a first passage with one or more inlet ports at an upstream side of the diverter that receive the flow of cryogen and two or more outlet ports at a downstream side of the diverter and in fluid communication with the heat exchanger.

11 Claims, 8 Drawing Sheets

CRYOSURGICAL INSTRUMENT WITH REDIRECTED FLOW

CROSS-REFERENCE TO RELATED APPLICATION

This application claims the benefit of priority from U.S. Provisional Patent Application No. 61/450,746, filed Mar. 9, 2011.

BACKGROUND

1. Technical Field

Embodiments of the present invention relate to cryosurgical equipment, and, more particularly, to cryoprobes or cryocatheters that feature a flow diverter that directs the incoming flow of cryogen against the inner wall of the external shaft thereof.

2. Description of Background Art

This description of background art is intended to provide the basic context of this patent application.

Cryoprobes that "boil" a liquid cryogen, when this liquid cryogen is supplied from an external source into the cryoprobe, are known for performing cryosurgical procedures. Generally, a cryogen is delivered into a cryoprobe in the form of a two-phase fluid, since a certain percentage of the liquid cryogen evaporates inevitably before entry to the cryoprobe as a result of imperfect thermal insulation of the delivery hose. This two-phase condition cannot easily be improved by separating the liquid and gaseous phases completely in the internal cavity of the cryotip (the distal section of the cryoprobe) without the implementation of special structures. In addition, in particular when nitrogen is used as a cryogen, the liquid nitrogen interacts with the solid, warmer surface by creating nitrogen gas cushion, known as Liedenfrost effect. This effect considerably reduces the ability to absorb heat from the warmer surface. Without addressing the problems caused by this cushion, it is impossible to take advantage of the boiling of the liquid fraction of the cryogen for effective freezing of a treated tissue. A more desirable solution would force the "boiling" of the liquid phase to take place as close as possible to the warmer surface.

Attempted solutions to these problems associated with using nitrogen as the cryogen are known; all suffer from significant drawbacks, however, due to the nature of boiling nitrogen fluid flow.

Joule-Thomson probes inherently operate such that the cryogen is delivered to an expansion chamber at the end of the tip, where it expands and cools. After cooling, the expanded and cooled cryogen then enters a return passage where it cools the external surface. When cooled by evaporation, the volume of the returning cryogen is considerably larger than the amount of cryogen initially supplied to the cryoprobe. Such an expanded volume of the return cryogen poses considerable difficulty for removal from the cryoprobe, due to the relatively small confines of the available exit(s) for exhausting the expanded cryogen.

BRIEF SUMMARY

This Summary is provided to introduce a selection of concepts in a simplified form that are further described below in the Detailed Description. This Summary is neither intended to identify key features or essential features of the claimed subject matter nor is it intended to be used to limit the scope of the claimed subject matter.

The background art does not provide a solution that overcomes the problem of exhausting a large, expanded volume of boiled, returning cryogen in the relatively small confines of the available exit(s) for exhausting the expanded cryogen.

Applicants have discovered an advantageous solution to the problems of the background art by adding a flow diverter which directs the incoming cryogen, entering the cryoprobe, directly towards the surface of the warmer external wall, and then causes the boiled cryogen to be exhausted from the cryoprobe through an inner return passage. The boiling of the cryogen at the inner surface of the external shaft of the cryoprobe, where heat exchange occurs, increases in volume and then increases the speed of the flow of the cryogen considerably, thus increasing the heat transfer from the inner surface of the external shaft to the cryogenic fluid. Bringing the two-phase cryogen, which contains larger portion of liquid phase, directly into contact with the internal surface of the outer wall cryoprobe, reduces the overall volume of the cryogen that is present at the heat exchange zone (which is also termed herein a heat exchange element). The size of the cross sectional area of the return channel (or channels) that is available to the return cryogen depends on the diameter of the probe.

At least one aspect of the present invention provides a cryosurgical instrument in which the flow diverter can be made of a rigid material such as metal or ceramic, or any other suitable material that maintains its structural integrity under the low temperature of the boiling cryogenic fluid and the resultant pressure of this material.

At least one aspect of the present invention provides a cryosurgical instrument in which a cryoprobe tip, which is situated near or in a central feeding tube of the cryoprobe and which, among many advantages, solves the above technical problem.

At least one aspect of the present invention provides a cryosurgical instrument in which the cryoprobe features a special tip, the flow diverting element and the heat exchanger, for forcing the cryogenic fluid to increase in speed and the liquid phase to come as close as possible to the inner surface of the external shaft. The special tip preferably features one or more mechanisms that increase the contact of the liquid phase with internal surface area of the external shaft and hence increase the heat transfer.

The special tip, in some aspects, is optionally and preferably constructed as a metal pipe with a suitable diameter to be introduced into the distal section of the central feeding tube. The proximal section of the metal pipe is preferably provided with straight or helical grooves, holes, other diffusion elements, or surface indentations directed outwards, thereby enabling this element to function as either a flow directing element, or a spraying component. In addition, the distal section of the tip, which is situated outside the central feeding tube, provides a limited cross section to force the cryogen to flow within a small film immediately on the inner surface of the cryoprobe.

Various implementations may optionally be used to install the special tip element in the central feeding tube. For example, the diameter of the element may optionally be of one tenth of a millimeter smaller than the inner diameter of the cryoprobe, such that the cryogenic fluid is directed toward the inner surface of the external shaft of the cryoprobe, then exhausted through an inner passage which acts as a return channel for the exhausted cryogen.

In addition, the distal section of the element may optionally be attached to the inner surface of the external shaft of the cryoprobe. Optionally a plurality of helical grooves are not attached to the inner surface so as to provide space for the boiling process to occur close to the inner surface of the external shaft, while the remaining surface in contact absorbs the heat by conduction.

One aspect of the present invention provides a cryosurgical instrument including: an external shaft with a cryotip at a distal end thereof; a cryogen supply tube at a proximal end of the external shaft, the supply tube supplying a cryogen to the instrument; a heat exchanger that cools a portion of the external shaft by directing the supplied cryogen against an inner surface of a portion of the external shaft and an inner surface of the tip and that guides exhausted cryogen away from the tip; and a flow diverter disposed between the cryogen supply tube and the heat exchanger. The flow diverter includes a first Y-configured passage with an inlet port at an upstream side of the diverter and a second Y-configured passage with an inlet port at a downstream side of the diverter, the first Y-configured passage receiving the supplied cryogen from the cryogen supply tube via the inlet port at the upstream side of the flow diverter and diverting the received cryogen to the heat exchanger in an downstream direction, and the second Y-configured passage receiving exhausted cryogen via the inlet port at the downstream side of the flow diverter and directing the received exhausted cryogen to an exhaust tube in a upstream direction.

Another aspect of the present invention provides a cryosurgical instrument including: an external shaft with a cryotip; a heat exchanger that cools a portion of the external shaft and the tip when cryogen is received thereby; and a flow diverter that receives a flow of cryogen, that splits the received flow of cryogen into two cryogen flows, and that delivers the split cryogen flows to the heat exchanger, the flow diverter including a Y-configured passage with an inlet port at an upstream side of the diverter that receive the flow of cryogen and two outlet ports at a downstream side of the diverter and in fluid communication with the heat exchanger.

Still another aspect of the present invention provides a cryosurgical instrument including: an external shaft with a cryotip; a heat exchanger that cools a portion of the external shaft and the tip when cryogen is received thereby; and a flow diverter that receives a flow of cryogen, that splits the received flow of cryogen into two or more split cryogen flows, and that delivers the split cryogen flows to the heat exchanger. The flow diverter includes a first passage with one or more inlet ports at an upstream side of the diverter that receive the flow of cryogen and two or more outlet ports at a downstream side of the diverter and in fluid communication with the heat exchanger.

These, additional, and/or other aspects and/or advantages of the present invention are: set forth in the detailed description which follows; possibly inferable from the detailed description; and/or learnable by practice of the present invention.

BRIEF DESCRIPTION OF THE DRAWINGS

The present invention will be more readily understood from the detailed description of embodiments thereof made in conjunction with the accompanying drawings of which.

DETAILED DESCRIPTION

Figure 1A:
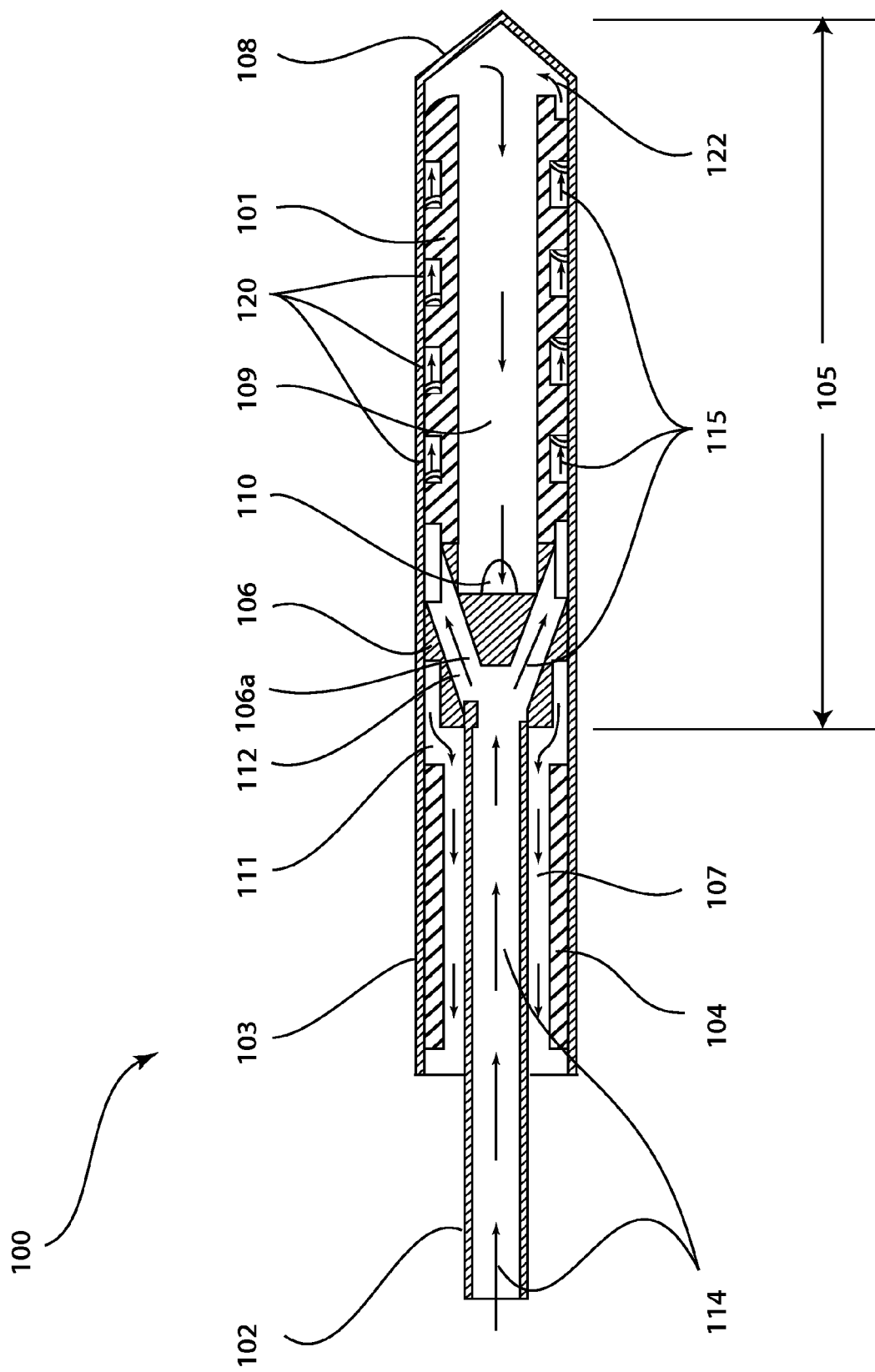
FIG. 1a is a longitudinal cross-section view of the cryoprobe consistent with an embodiment of the present invention, with a spiral heat-exchanging element, showing inlet passages of the flow-diverting element.

Reference will now be made in detail to embodiments of the present invention, examples of which are illustrated in the accompanying drawings, wherein like reference numerals refer to the like elements throughout. The embodiments are described below to explain the present invention by referring to the figures.

Although the following text sets forth a detailed description of at least one embodiment or implementation, it is to be understood that the legal scope of protection of this application is defined by the words of the claims set forth at the end of this disclosure. The detailed description is to be construed as exemplary only and does not describe every possible embodiment since describing every possible embodiment would be impractical, if not impossible. Numerous alternative embodiments and/or implementations are both contemplated and possible, using either current technology or technology developed after the filing date of this patent, which would still fall within the scope of the claims.

It is to be understood that, unless a term is expressly defined in this application using the sentence "As used herein, the term" is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

The term "cryosurgical instrument" refers herein to any type of cryo-instrument including, but not limited to, cryoprobes and cryocatheters. Although the description centers around cryoprobes, this is for the purpose of illustration only and is without any intention of being limiting.

Figure 1B:
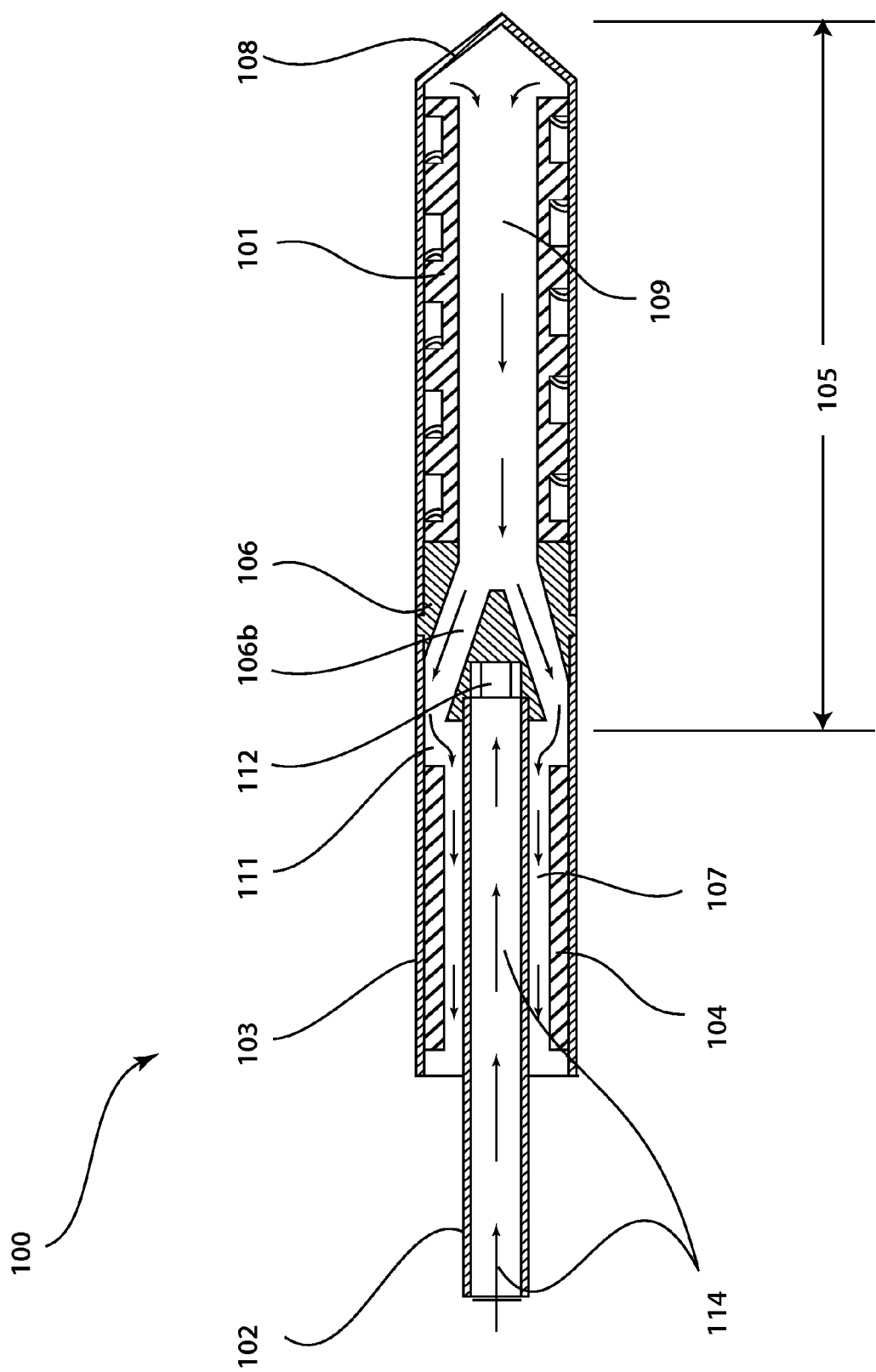
FIG. 1b is a longitudinal cross-section view of the cryoprobe of FIG. 1a, with a spiral heat-exchanging element, showing outlet passages of the flow-diverting element.
Figure 1C:
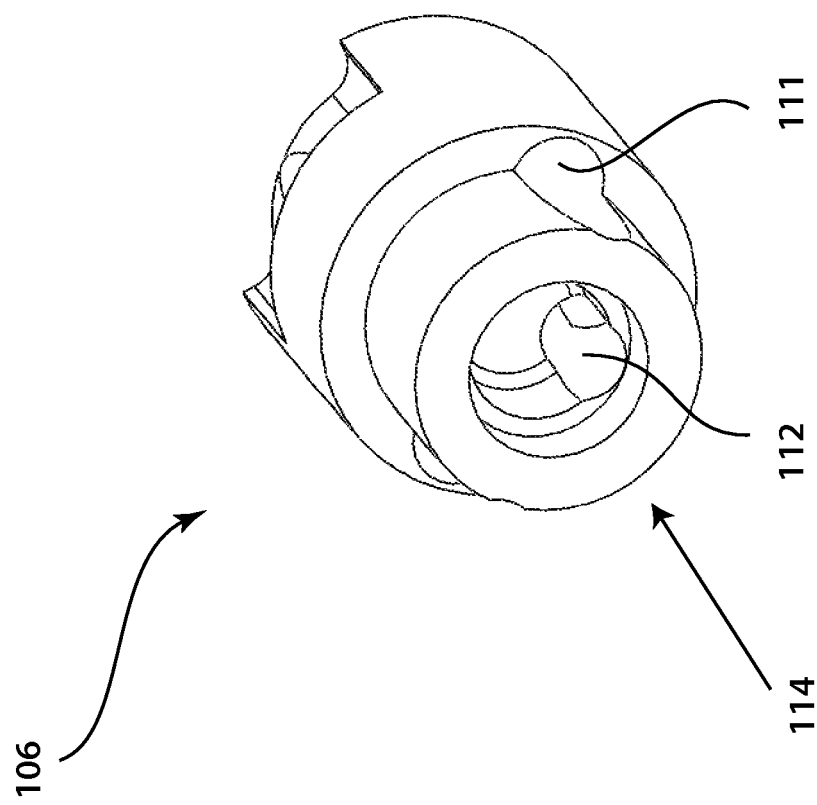
FIG. 1c is a front, perspective view of the flow diverter 106 of FIGS. 1a and 1b.
Figure 1D:
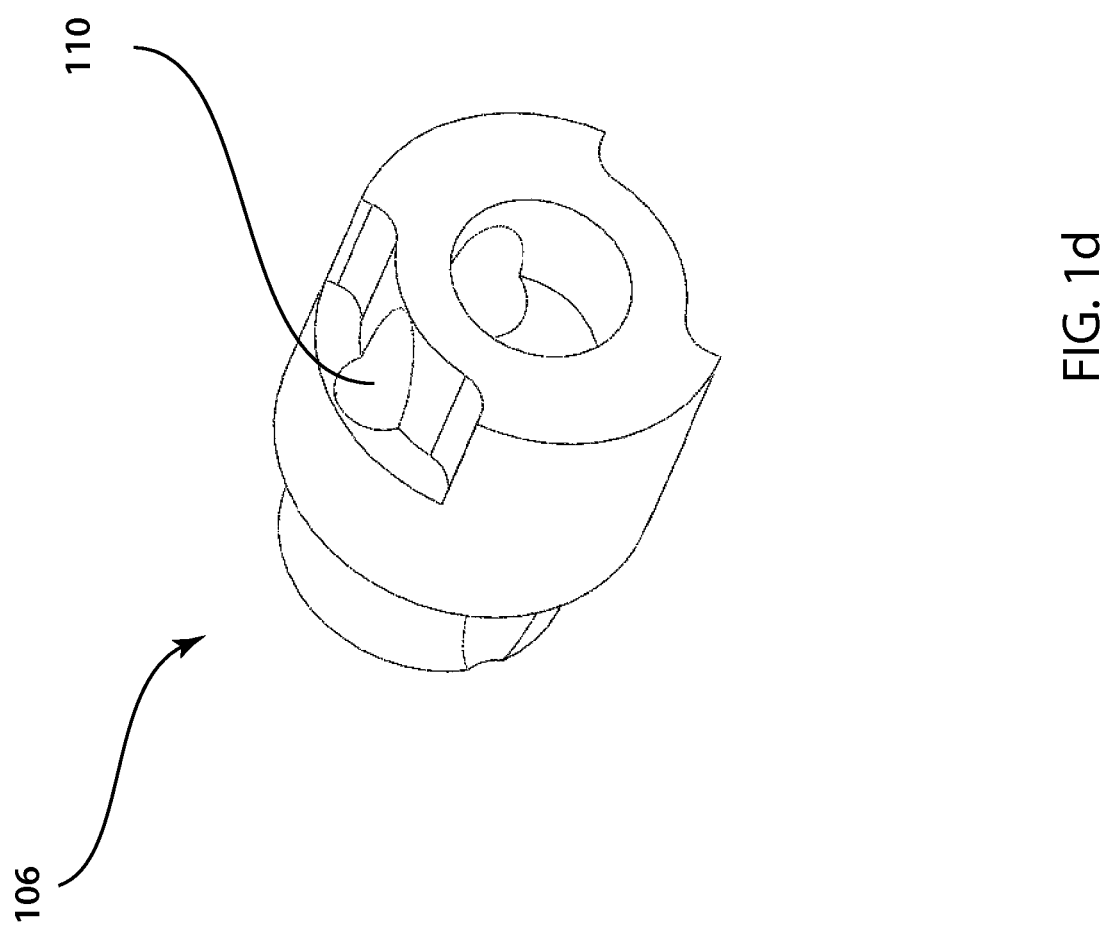
FIG. 1d is a rear, perspective view of the flow diverter 106 of FIGS. 1a and 1b.

Referring to FIGS. 1a-1d, FIG. 1a is a longitudinal cross-section of a cryoprobe 100 with a spiral heat exchanger, showing the inlet passages. FIG. 1b is a longitudinal cross-section of the cryoprobe with a spiral heat exchanger, showing the outlet passages, which is a 90-degree rotational view of the view in FIG. 1a. FIGS. 1c and 1d are perspective views of the flow diverter 106 of FIGS. 1a and 1b.

The cryoprobe 100 comprises an external shaft 103 and, from upstream to downstream, a cryogen supply tube 102 at a proximal end of the cryoprobe, a flow diverter 106, a heat exchanger 101, and a tip 108 at a distal end of the cryoprobe.

The cryogen supply tube 102 delivers cryogen to the cryoprobe 100 and may generally be disposed centrally, along a longitudinal axis (not shown) of the cryoprobe. The cryogen supply tube 102 is in fluid communication with the flow diverter 106, which is in fluid communication with the heat exchanger 101.

The flow diverter 106 diverts the incoming flow of cryogen 114 from the cryogen supply tube 102 and is located within the external shaft 103. In more detail, the flow diverter serves to direct the incoming flow from the center of the cryosurgical device to the outer surface of the cryosurgical device. That is to say to the inner surface of external shaft 103. Preferably, the flow diverter 106 is centrally disposed along the longitudinal axis (not shown) of the cryoprobe 100. This position encourages symmetrical delivery of the cryogen to the heat exchanger 101, as explained below.

The flow diverter 106 preferably comprises two-Y type (i.e., Y configured) passages 106a, 106b located in a 90-degree rotational relationship to one another and placed in opposite directions. This is to say that each of the passages has a single port at one end and two ports at another opposing other. FIG. 1a shows the inlet fluid Y passage 106a and the FIG. 1b shows the return fluid Y passage 106b. This configuration is exemplary; other configurations are both contemplated and possible.

For example, in one contemplated variation, instead of Y-type passages, the flow diverter 106 may have passages with a single, central inlet port and multiple (i.e., more than two) peripheral outlet ports. Further, these outlet ports may be spaced evenly around the periphery of the flow diverter to promote even diversion of the cryogen flow against the external shaft 103.

In another contemplated variation, the passages 106a and 106b of the flow diverter 106 need not share the same configuration. Also, the respective outlet ports of the passages 106a and 106b need not be circular. Rather, they may be elliptical or slotted.

In yet another contemplated variation, the flow passages 106a and 106b of the flow diverter 106 may have multiple inlets and multiple outlets.

In sum, the inventors contemplate multiple combinations of inlet ports and outlet ports of the flow passages, as well as multiple configurations of the passages, depending on, inter alia, desired performance and the flow and cooling properties of the specific cryogen being used.

The heat exchanger 101 is located within an external shaft 103 and directs cryogen against an inner surface of external shaft 103. To achieve this direction of the cryogen flow 114, the heat exchanger is provided with a plurality of grooves 120, of which two are shown for the purpose of description only, which are close to the inner surface of the external shaft 103. The spiral grooves 120 spiral about the longitudinal axis of the cryoprobe 100 and are open to the inner surface of the external shaft 103. That is to say that the grooves 120 are in fluid communication with the inner surface of the external shaft 103. The two-phase cryogen flows in the spiral groove 120 and boils between the heat exchanger 101 and the inner surface of the external shaft 103, increasing its speed and enhancing the heat transfer between the cryoprobe 100 and the cryogen.

In operation, the cryogen supply tube 102 introduces cryogen into the device 100 and directs the flow 114 of the cryogen through an inlet port 112 and then into the inlet fluid Y passage 106a of the flow diverter 106. Thereafter, the flow of cryogen passes through the inlet fluid Y passage 106a and into the heat exchanger 101.

Next, cryogen flows from the inlet fluid Y passage 106a to each of a plurality of open spiral grooves 120. The spiral grooves 120 exhaust the spiraling flow of cryogen 115 against an inner surface 122 of the tip 108. Then, the flow of cryogen, after being reflected by the inner surface 122, enters the inner passage 109 within the heat exchanger 101. After this reflection, the cryogen may be characterized as expanded/exhausted.

Thereafter, the expanded cryogen enters a return port 110 of the flow diverter 106, flows through return fluid Y passage 106b to a return passage 111 and then to the exhaust tube 107. The exhaust tube 107 is located between an optional insulation sleeve 104 and the cryogen supply tube 102. The insulation sleeve 104 is near the proximal end of the cryoprobe 100. Thermal insulation sleeve 104 terminates the heat transfer (ablation) zone 105 of the cryoprobe 100.

The length of the cryoprobe 100 between the tip 108 and the insulation sleeve 104 defines an ablation zone 105. That is to say the ablation zone 105 is defined by a non-insulated inner surface of the cryoprobe 100 that comes in contact with the boiling cryogen.

Figure 2A:
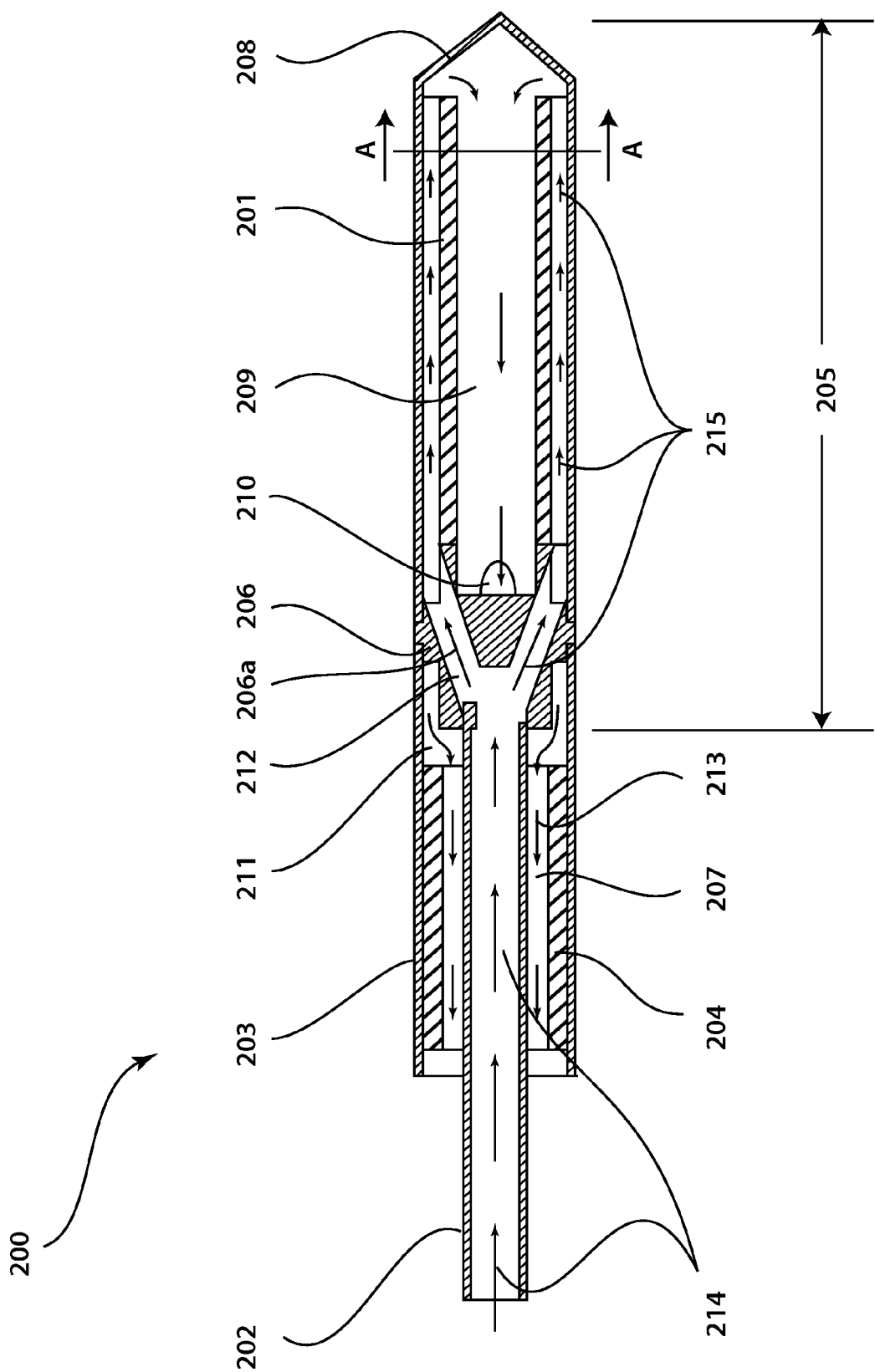
FIG. 2a is longitudinal cross-section view of the cryoprobe consistent with an embodiment of the present invention, with external straight grooves provided for inlet flow, showing inlet passages of the flow diverter.
Figure 2B:
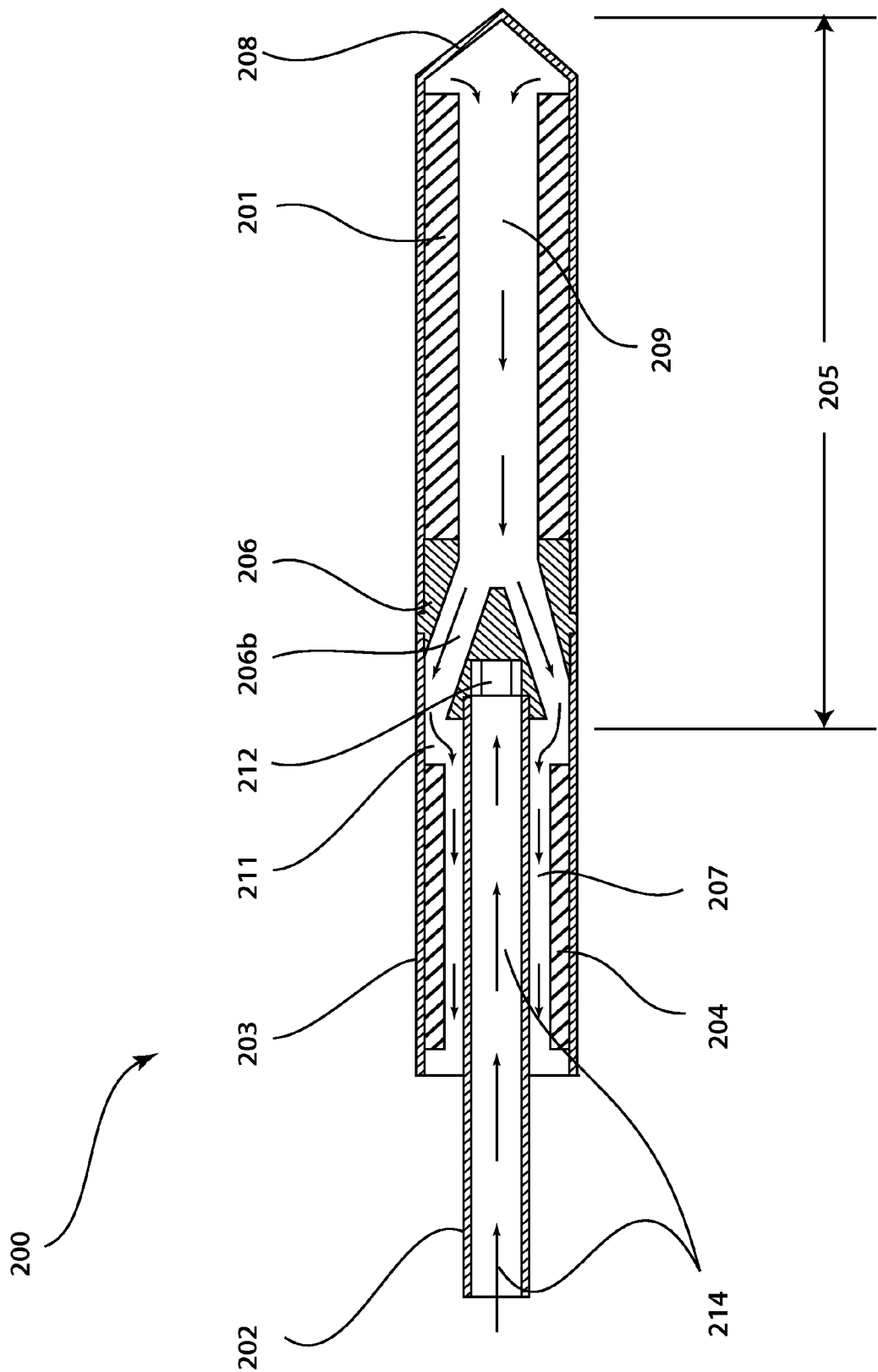
FIG. 2b is longitudinal cross-section view of the cryoprobe of FIG. 2a with external straight grooves provided for outlet flow.
Figure 2C:
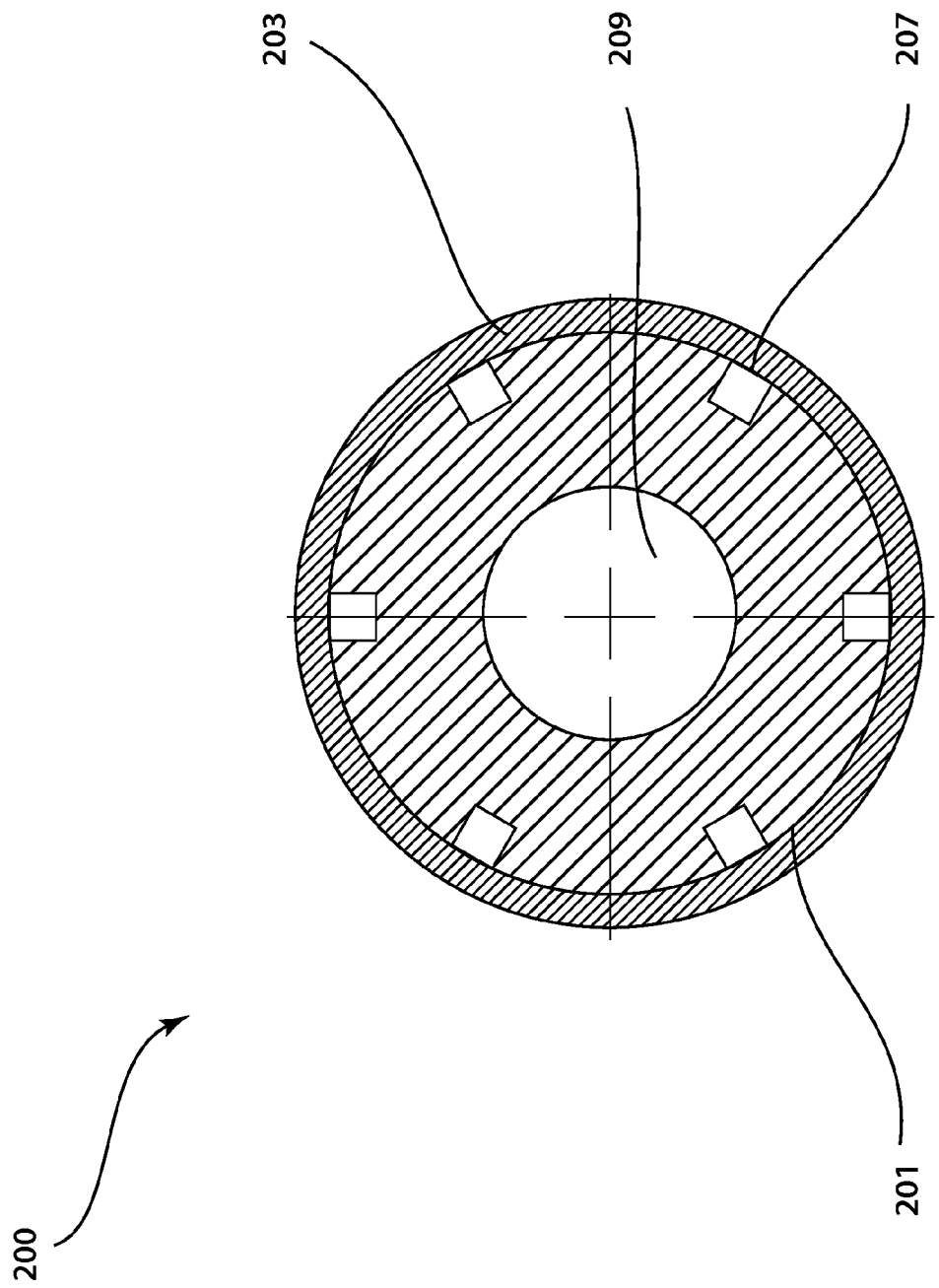
FIG. 2c is a lateral cross-section of the cryoprobe of FIG. 2a along line A-A, with external grooves provided.

Referring to FIGS. 2a-2c, FIG. 2a is longitudinal cross-section of a cryoprobe 200 with external straight grooves provided for inlet flow, showing the inlet passages. FIG. 2b is a longitudinal cross-section of the cryoprobe 200 with external straight grooves provided for outlet flow, which is a 90-degree rotational view of the view in FIG. 2a. FIG. 2c is a lateral cross-section of the cryoprobe 200 of FIG. 2a along line A-A, showing the radial dispersal of the straight grooves of the heat exchanger.

Elements with the same or similar function as elements in FIGS. 1a-1d are identified by similar reference numbers.

The cryoprobe 200 comprises a flow diverter 206, and heat exchanger 201, which ends at its distal end in a hollow, closed tip 208. Cryoprobe 200 operates in a manner similar to that of cryoprobe 100 of FIGS. 1a-1d, except that heating exchanging element 201 features open linear grooves 221, rather than the open spiral grooves 120 shown in FIGS. 1a and 1b. FIG. 2c shows the configuration of exhaust tube 207 in more detail; a similar configuration may also be made for exhaust tube 107 of cryoprobe 100 as shown in FIGS. 1a-1d.

The heat exchanger 201 is located within an external shaft 203 and directs cryogen against an inner surface of external shaft 203. External shaft 203 is preferably insulated with an insulation sleeve 204. Tip 208 closed the external shaft 203 at a distal end thereof.

A central cryogen supply tube 202, located at least partially within external shaft 203 at its proximal end, supplies a flow of cryogen 214 to a flow diverter 206. This flow 214 enters the flow diverter 206 through an inlet port 212.

Flow diverter 206 preferably comprises two-Y type passages located in a 90-degree rotational relationship to one another, placed in opposite directions within external shaft 203. FIG. 2a shows the inlet fluid Y passage 206a and the FIG. 2b shows the return fluid Y passage 206b. This configuration is exemplary; other configurations are both contemplated and possible.

In operation, cryogen flows from inlet port 212, through the Y passage 206a, to one of a plurality of external straight grooves 221. The straight grooves 221 extend in parallel to the longitudinal axis of the cryoprobe 200 and are close to the inner surface of the external shaft 203. The flow of cryogen 215 continues to the ends of the grooves 221 where the returning, expanded cryogen, is reflected by an inner surface of tip 208, enters the inner passage of the heat exchanger 209. The two-phase cryogen flows in the grooves 221 and boils between the heat exchanger 201 and the inner surface of the external shaft 203, increasing its speed and enhancing the heat transfer between the cryoprobe 200 and the cryogen.

Thereafter, the cryogen then enters a return port 210, flowing through Y passage 206b to a return passage 211, then to the exhaust tube 207. The flow of the cryogen is indicated by reference numeral 213.

Figure 3:
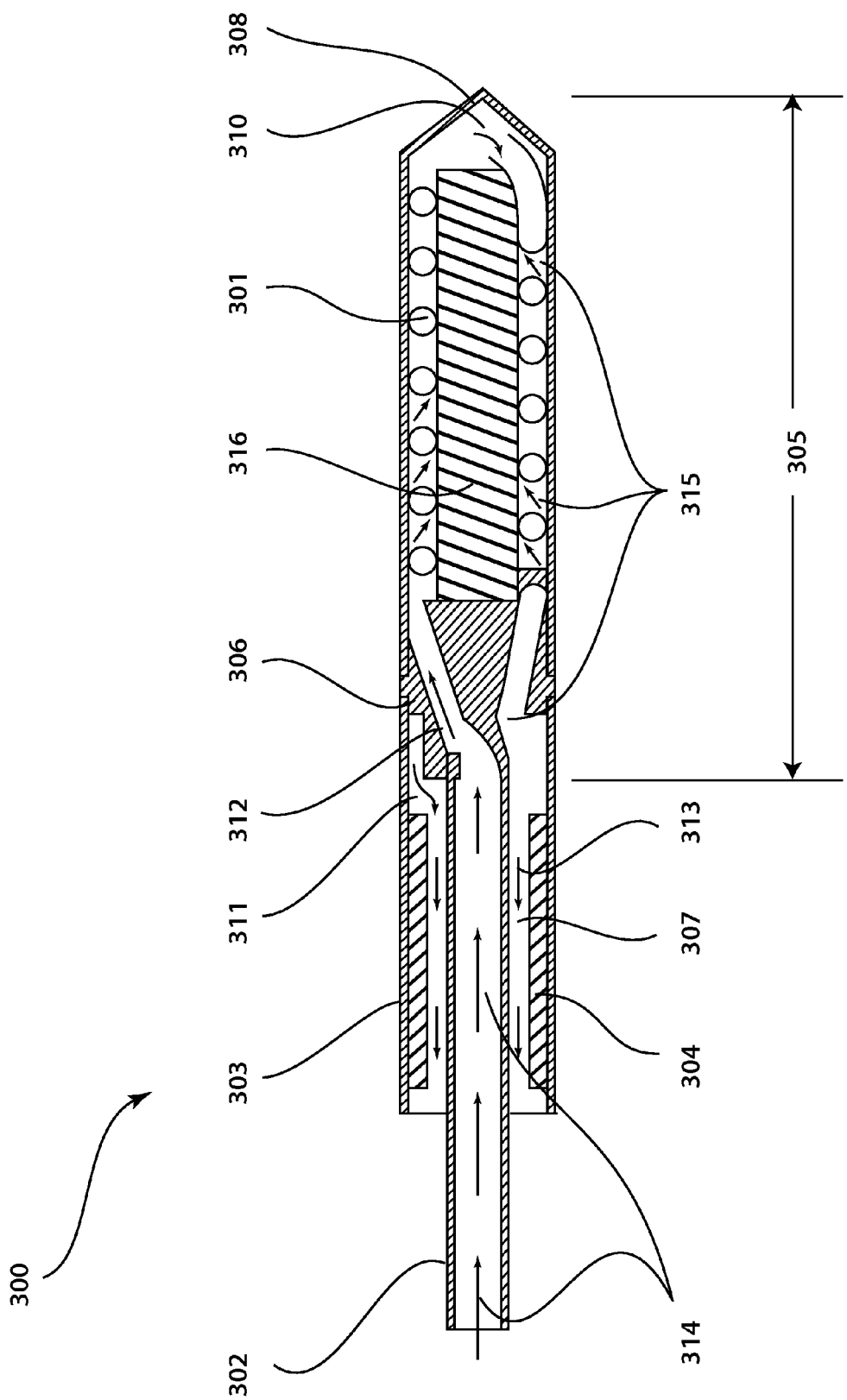
FIG. 3 is a longitudinal cross section of a cryoprobe consistent with an embodiment of the present invention, with a spiral heat exchanger.

FIG. 3 is a longitudinal cross-section of a cryoprobe 300 consistent with another aspect of the present invention, with an internal spiral coil provided for outlet-flow by the arrangement of a heat exchanger 301. Elements with the same or similar function as elements in FIGS. 1a-1d are identified by similar reference numbers.

In operation, the cryogen flow 314 enters from the cryogen supply tube 302 and enters a flow diverter 306. The cryogen is forced through the gap between the heat exchanger 301 and the external shaft 303, through an inlet port 312 from flow diverter 306. Heat exchanger 301 is shown as featuring a spiral coil configuration spiraling about the longitudinal axis of the cryoprobe 300. After cooling the surface of the external shaft 303 along the ablation zone 305, the cryogen reaches the tip 308. The cryogen is then reflected and, through one or more openings 310, of which one is shown for the purpose of illustration only, the flow 313 enters into heat exchanger 301, reaching the exhaust tube 307 via the return cryogen passage 311. To prevent the return cryogen to flowing in a retrograde manner, preferably a filling element 316 fills the volume inside the spirals of the coils of the heat exchanger 301.

The exhaust tube 307 is located between an optional insulation sleeve 304 and the cryogen supply tube 302. The insulation sleeve 304 is near the proximal end of the cryoprobe 300. Thermal insulation sleeve 304 terminates the heat transfer zone 305 of the cryoprobe 300.

The length of the cryoprobe 300 between the tip 308 and the insulation sleeve 304 defines an ablation zone 305. That is to say the ablation zone 305 is defined by a non-insulated inner surface of the cryoprobe 300 that comes in contact with the boiling cryogen.

As the foregoing evidences, Applicants have discovered an innovative approach to directing an incoming flow of liquid cryogen in a cryosurgical device by adding a novel flow diverter. The flow diverter directs the incoming cryogen directly towards the surface of the external wall of the cryosurgical device, which is a relatively warm surface. This promotes boiling of the cryogen. Also, the flow diverter facilitates the exhaust of the boiled cryogen from the cryoprobe through an inner return passage in the element.

Examples of various features/aspects/components/operations have been provided to facilitate understanding of the disclosed embodiments of the present invention. In addition, various preferences have been discussed to facilitate understanding of the disclosed embodiments of the present invention. It is to be understood that all examples and preferences disclosed herein are intended to be non-limiting.

Although selected embodiments of the present invention have been shown and described individually, it is to be understood that at least aspects of the described embodiments may be combined.

Also although selected embodiments of the present invention have been shown and described, it is to be understood the present invention is not limited to the described embodiments. Instead, it is to be appreciated that changes may be made to these embodiments without departing from the principles and spirit of the invention, the scope of which is defined by the claims and the equivalents thereof.

What is claimed is:

1. A cryosurgical instrument comprising:
an external shaft with a cryotip at a distal end thereof;
a cryogen supply tube at a proximal end of the external shaft, the supply tube supplying a cryogen to the instrument;
a heat exchanger that cools a portion of the external shaft by directing the supplied cryogen against an inner surface of a portion of the external shaft and an inner surface of the cryotip and that guides exhausted cryogen away from the cryotip; and
a flow diverter disposed within the external shaft and between the cryogen supply tube and the heat exchanger, the flow diverter including
a first Y-configured passage with an inlet port at an upstream side of the diverter and
a second Y-configured passage with an inlet port at a downstream side of the diverter,
the first Y-configured passage receiving the supplied cryogen from the cryogen supply tube via the inlet port at the upstream side of the flow diverter and diverting the received cryogen to the heat exchanger in a downstream direction, and
the second Y-configured passage receiving exhausted cryogen via the inlet port at the downstream side of the flow diverter and directing the received exhausted cryogen to an exhaust tube in an upstream direction.

2. The cryosurgical instrument of claim 1, wherein the heat exchanger includes an inner passage extending from an end thereof proximate to the inner surface of the cryotip to the downstream side of the flow diverter and through which the exhausted cryogen flows away from the cryotip, and wherein the inlet port of the second Y-configured passage is in fluid communication with the inner passage.

3. The cryosurgical instrument of claim 1, wherein the heat exchanger comprises a plurality of grooves that spiral about a longitudinal axis of the heat exchanger and that open to portions of the inner surface of the external shaft.

4. The cryosurgical instrument of claim 1, wherein said heat exchanger comprises a plurality of straight grooves that extend in parallel to a longitudinal axis of the heat exchanger.

5. The cryosurgical instrument of claim 1, wherein the Y-configured passages are in a mutual 90-degree rotational relationship to one another.

6. The cryosurgical instrument of claim 1, wherein said heat exchanger includes a spiral coil that spirals about a longitudinal axis of the cryosurgical instrument, is in contact with a portion of the inner surface of the external shaft,
forms one or more first spiral channels that, in cooperation with the external shaft, direct the flow of cryogen from the flow diverter to the cryotip, and
forms one or more second spiral channels that, in cooperation with the external shaft, direct the flow of exhausted cryogen from the cryotip to the flow diverter.

7. The cryosurgical instrument of claim 6, further comprising a filling element that fills a volume inside of the spirals so as prevent the return cryogen to flowing in a retrograde manner.

8. The cryosurgical instrument of claim 1, wherein the flow diverter is formed of a unitary workpiece.

9. A cryosurgical instrument comprising:
an external shaft with a cryotip at a distal end thereof;
a cryogen supply tube at a proximal end of the external shaft, the supply tube supplying a cryogen to the instrument;
a heat exchanger that cools a portion of the external shaft by directing the supplied cryogen against an inner surface of a portion of the external shaft and an inner surface of the cryotip and that guides exhausted cryogen away from the cryotip; and a flow diverter disposed between the cryogen supply tube and the heat exchanger, the flow diverter including
 a first Y-configured passage with an inlet port at an upstream side of the diverter and
 a second Y-configured passage with an inlet port at a downstream side of the diverter, the first Y-configured passage receiving the supplied cryogen from the cryogen supply tube via the inlet port at the upstream side of the flow diverter and diverting the received cryogen to the heat exchanger in a downstream direction, and the second T-configured passage receiving exhausted cryogen via the inlet port at the downstream side of the flow divert and directing the received exhausted cryogen to an exhaust tube in an upstream direction, wherein the first Y-configured passage includes a single branch portion with one end at the inlet at the upstream side of the flow diverter and with an opposing end that splits into two branch portions, and wherein the second Y-configured passage includes a single branch portion with one end at the inlet at the downstream side of the flow diverter and with an opposing end that splits into two branch portions.

10. A cryosurgical instrument comprising:

an external shaft with a cryotip;

a heat exchanger that cools a portion of the external shaft and the cryotip when cryogen is received thereby; and a flow diverter that receives a flow of cryogen, that splits the received flow of cryogen into two cryogen flows, and that delivers the split cryogen flows to the heat exchanger, the flow diverter including a Y-configured passage with an inlet port at an upstream side of the diverter that receives the flow of cryogen and two outlet ports at a downstream side of the diverter, and that is in fluid communication with the heat exchanger, wherein the heat exchanger further comprises a pathway that guides exhausted cryogen away from the cryotip, and wherein the flow diverter includes a second Y-configured passage with an inlet port at the downstream side of the diverter and that is in fluid communication with the pathway of the heat exchanger and two outlet ports at the upstream side of the diverter.

11. A cryosurgical instrument comprising:

an external shaft with an inner surface and a cryotip;

a heat exchanger that cools a portion of the external shaft and the cryotip when cryogen is received thereby, the heat exchanger includes an internal passageway that guides exhausted cryogen away from the cryotip; and a flow diverter that receives a flow of cryogen, that splits the received flow of cryogen into two or more split cryogen flows, and that delivers the split cryogen flows to the heat exchanger, the flow diverter including a first passage with one or more inlet ports at an upstream side of the diverter that receive the flow of cryogen and two or more outlet ports at a downstream side of the diverter and in fluid communication with the heat exchanger, wherein the heat exchanger is configured (i) to direct the delivered split flow of cryogen from the flow diverter to the cryotip and (ii) to cool the inner surface of the external shaft with the split flow as that flow travels to the cryotip, and wherein the exhausted cryogen travels from the cryotip to the flow diverter only through the internal passageway of the heat exchanger.

* * * * *